United States Patent [19]

Yuasa et al.

[11] Patent Number: 5,753,428

[45] Date of Patent: May 19, 1998

[54] SYNTHETIC COMPOSITION FOR STORAGE OF PLATELETS COMPRISING GLYCEROL

[75] Inventors: Takeshi Yuasa, Ohita-ken; Hitoshi Ohto, Hukushima, both of Japan

[73] Assignee: Kawasumi Laboratories, Inc., Tokyo, Japan

[21] Appl. No.: 679,271

[22] Filed: Jul. 12, 1996

[30] Foreign Application Priority Data

Jul. 19, 1995 [JP] Japan .................. 7-205300
Jun. 21, 1996 [JP] Japan .................. 8-181303

[51] Int. Cl.⁶ .................................................. A01N 1/02
[52] U.S. Cl. .................................. 435/2; 424/93.72
[58] Field of Search ..................... 435/2; 424/93.72

[56] References Cited

U.S. PATENT DOCUMENTS 4,992,363  2/1991  Murphy ........................ 435/2
5,376,524  12/1994  Murphy et al. ............... 435/2

Primary Examiner—Sandy Saucier
Attorney, Agent, or Firm—Michael J. Striker

[57] ABSTRACT

The platelet preservation solution does not containing any plasma proteins but includes 5 to 100 mM of glycerol, from 5 to 15 mM of sodium citrate, from 10 to 30 mM of sodium acetate, from 10 to 50 mM of disodium hydrogen phosphate, up to 10 mM of citric acid, up to 50 mM of glucose and from 50 to 150 mM of electrolyte compounds in addition to the sodium acetate, disodium hydrogen phosphate and sodium citrate. The electrolyte compounds include sodium chloride. The artificial platelet preservation solution prevents adverse reactions caused by plasma components resulting in a greater platelet survival ratio during storage.

4 Claims, No Drawings

SYNTHETIC COMPOSITION FOR STORAGE OF PLATELETS COMPRISING GLYCEROL

BACKGROUND OF THE INVENTION

1. Field of the Invention

This invention relates to an artificial preservation solution for platelets, which can replace plasma components in blood platelet products.

2. Prior Art

A high unit blood platelet product used for the patients who need blood platelet transfusion has been prepared by the platelet apheresis of the donated blood and the Japan Red Cross Corp. is supplying 5–20 units. (1 unit; 200 ml)

The blood platelet product is a suspension of the blood platelets in plasma. As a result, adverse reactions such as allergy, edema, dyspnea, pyrexia and urticaria occur among patients who frequently receive transfusion of the blood platelet products. It is a problem that the blood platelet transfusion is not effective for patients who are hypersensitive, because it is necessary to stop the transfusion at 5–10 ml. On the other hand, the plasma, a known preservation solution of the blood platelet is the raw material for the plasma fractionated products (cryo products, No. XIII factor products, globulin products, etc.) and the effective utilization and the increase of the supply of the raw material plasma are needed.

SUMMARY OF THE INVENTION

The object of the present invention is to provide an artificial preservation solution for blood platelets having an equivalent preservation ability to the existing preservation solution consisting of the plasma. The adverse reactions during transfusion caused by the plasma proteins are prevented and the effective utilization and the increase of the supply of the raw material plasma used for the plasma fraction products are achieved when the preservation solution according to the invention is used. For the achievement of the above object, the present invention provides a physiologically adaptable preservation solution for blood platelets comprising following components in the physiological saline solution (NaCl).

disodium hydrogen phosphate: 10–50 mM sodium acetate: 10–15 mM sodium citrate: 5–30 mM citric acid: 0–10 mM glucose: 0–5 mM membrane permeable polyhydric alcohol: 5–100 mM electrolytes: 50–150 mM In the preservation solution of the platelet according to the present invention, disodium hydrogen phosphate acts as the buffer for the pH together with sodium citrate, citric acid and sodium acetate, maintains the pH of the solution in a range from 6.5 to 8.0, preferably from 6.7 to 7.5 and prevents the lowering of the pH of the solution caused by the production of the organic acids lactic acid, etc.) by the anaerobic metabolism of the platelet. The production of lactic acid in 5 days preservation period of the platelet in the preservation solution of the platelet amounts to ca. 20 mM at the maximum and 10–50 mM of disodium hydrogen phosphate, preferably 25–40 mM, is required to prevent the resulting lowering of the pH. It is said that the platelet can usually function in the neutral pH range, 6.5–8.0. The pH below 6.5 or above 8.0 is not preferable because it is reported that the platelet loses its original function by the lowering of its aggregation ability.

Sodium acetate is used to promote aerobic metabolism of the platelet and prevent the formation of lactic acid. Sodium citrate is used to prevent the aggregation of the platelet and citric acid plays a role as a buffer of the pH or controlling agent. Citric acid is added as a buffer solution in phosphoric acid-citrate acid system, however, there are cases in which the adjustment of the pH by its addition is not needed depending on the concentration of disodium hydrogen phosphate, when the pH of the solution is adjusted to 7.4, which is preferable for the preservation solution of the platelet.

Glucose is contained as an energy resource of the platelet and maintains the platelet functions such as stability of the membrane and the survival ratio by producing high energy phosphate compound ATP (adenosine-3-phosphate)

Membrane permeable polyhydric alcohol is used to stabilize the platelet membrane during the preservation period and it is preferable to use glycerin which can protect cells, organ species and blood cell components from damage by freezing.

The electrolytes are used to maintain the solution isotonic and it is preferable to use one kind or more than two kinds of ion selected from the group consisting of $Na^+$, $K^+$, $Mg^{2+}$ and $Cl^-$.

It is preferable to adjust the ratio of the osmotic pressure of the preservation solution of the present invention to the physiological saline solution (osmotic pressure; 280–285 mOsms)

The ratio of the osmotic pressure of the platelet preservation solution to that of a normal saline solution effects the preservation status of the platelet through the membrane of the platelet. When the ratio is below 0.5, significant swelling of the platelet occurs and above 2.0, significant shrinking of the platelet occurs and this is not preferable because of the decrease of the aggregation ability and flexibility of the membrane.

DESCRIPTION OF THE PREFERRED EMBODIMENT

Example 1

400 ml of blood was gathered in a blood bag made of polyvinyl chloride containing 5.6 ml of anticoagulant CPD solution (a mixture of citrate, phosphate and dextrose) and by a weak centrifuge treatment, PRP (platelet rich plasma) was obtained as an upper layer component. The first subsidiary bag (vacant) is connected germ freely to the blood bag. After transferring PRP in the blood bag to the subsidiary bag, the platelet pellet is obtained in the lower layer in the subsidiary bag by a strong centrifuge treatment. The second subsidiary bag (vacant) is connected to the first subsidiary bag germ freely and the supernatant plasma was transferred to the second bag. Then the platelet preservation solution in Table 1 is added germ freely to the platelet in the first subsidiary bag and the volume was adjusted to 40 ml.

In Table 1, the composition of the platelet preservation solution used in Ex 1 and 2 (examples 1 and 2) are the ones according to the present invention and the composition of the platelet preservation solution in the Comp 1 (comparative example) is different from the composition of the present invention.

TABLE 1

| Composition of artificial platelet solutions (mM) | | | |
|---|---|---|---|
|  | Ex 1 | Ex 2 | Comp 1 |
| NaCl | 90 | 90 | 90 |
| KCl | 5 | 5 | 5 |

TABLE 1-continued

| Composition of artificial platelet solutions (mM) | | | |
|---|---|---|---|
| | Ex 1 | Ex 2 | Comp 1 |
| $MgCl_2$ | 3 | 3 | 3 |
| $NaH_2PO_4$ | — | — | 4.9 |
| $Na_2HPO_4$ | 33 | 33 | 20.1 |
| Na acetate | 25 | 25 | 23 |
| $Na_3$ citrate | 15 | 15 | 17 |
| Citric acid | 2 | 2 | — |
| Maltose | — | — | 28.8 |
| Glucose | — | 25 | 23.5 |
| Glycerin | 50 | 25 | — |
| pH | 7.3 | 7.3 | 7.3 |
| Osmolality(mOsm) | 392 | 392 | 430 |

After adding each platelet preservation solution in Table 1 to platelet pellet, each platelet pellet was maintained at room temperature for about 1 hr and then the pellet was floated by stirring (55 strokes/min.) using a horizontal shaking device. As a Comparative example (Comp 2), 40 ml of the platelet concentration solution (PC), which is a dispersion of the platelet in the plasma and most preferable plasma preservation solution, if it does not cause adverse reactions, such as allergic reactions in patients was placed in a different subsidiary bag.

The platelet solution of Ex 1 and 2, Comp 1 and 2 were preserved for several days. On day 3 and 5, various kinds of tests on the preservation ability was conducted using samples taken from the bag germ freely by connecting operation adapter to the transfusion outlet of the bag. The results are shown in Table 2.

The platelet metabolizes aerobically during the preservation and as a result lactic acid is produced and the pH is lowered. It is said that the aggregation ability and the survival ratio after transfusion is affected by the lowering of the platelet function, when the pH is significantly low (below 6.5). It is considered that the amount of lactic acid production during the preservation period of the platelet could be a measure of the ratio of anaerobic glucose metabolism of the platelet. On day 3 of the preservation, there were no differences between Ex 2, Comp 1 and 2, however, on Day 5, the suppression of the metabolism of Ex 2 was lower than that of Comp 1 and equal to that of the Comp 2 (the platelet preserved in the plasma). Since Ex 1 does not contain glucose, the production of lactic acid was suppressed at a lower level except that a small amount of the original CPD solution remains in the preservation solution.

As to the pH maintaining effect, Ex 2 maintained higher pH value compared with Comp 1 (near the level of the Comp 2) and it was confirmed that the deterioration (activation) of the platelet caused by low pH is suppressed.

There were no significant differences in the platelet aggregation ability among Ex 1 and 2, Comp 1 and 2 at a high concentration of the aggregation inducing material (collagen 10 μg/ml, ADPI 10 μg/ml), however, at a lower concentration (collagen 5 μg/ml), Ex 2 had excellent aggregation ability showing the same ability as that of Comp 2.

In the low osmotic pressure shock recovery test (%HSR), on day 3 of the preservation, Ex 2 showed higher %HSR than that of Comp 2 and on day 5 of the preservation, Ex 1 and 2 and Comp 1 and 2 showed the same tolerance level to the low osmotic pressure. The morphology of the platelet in Ex 2 was better than that of Comp 2 on day 3 of the preservation, however, on day 5, there was no difference

TABLE 2

| Platelet function during the preservation | | | | | |
|---|---|---|---|---|---|
| | Days of the preservation | Ex 1 | Ex 2 | Comp 1 | Comp 2 |
| pH | 3 | 6.76 ± 0.02 | 6.99 ± 0.03 | 6.87 ± 0.13 | 7.20 ± 0.06 |
| | 5 | 6.70 ± 0.05 | 6.87 ± 0.04 | 6.71 ± 0.13 | 7.03 ± 0.07 |
| Platelet numbers | 3 | 136 ± 17 | 136 ± 19 | 107 ± 16 | 115 ± 12 |
| ($10^7$/ml) | 5 | 137 ± 19 | 132 ± 20 | 107 ± 18 | 111 ± 11 |
| Mean platelet volume (fl) | 3 | 7.9 ± 0.5 | 7.5 ± 0.5 | 7.9 ± 0.2 | 8.0 ± 0.3 |
| | 5 | 8.5 ± 0.5 | 7.9 ± 0.3 | 8.1 ± 0.3 | 8.3 ± 0.4 |
| Glucose | 3 | 9.1 ± 1.7 | 378 ± 18 | 388 ± 19 | 400 ± 20 |
| (mg/dl) | 5 | 6.7 ± 1.1 | 327 ± 17 | 320 ± 30 | 315 ± 27 |
| Lactic acid production | 3 | 4.4 ± 1.0 | 7.3 ± 1.5 | 7.2 ± 1.2 | 7.6 ± 0.2 |
| amount (mmol/l) | 5 | 4.2 ± 1.1 | 13.2 ± 2.1 | 16.3 ± 4.5 | 12.3 ± 2.4 |
| β-thromboglobulin | 3 | 11.5 ± 3.3 | 9.3 ± 2.0 | 12.2 ± 2.7 | 8.5 ± 2.2 |
| (μg/ml) | 5 | 19.1 ± 4.1 | 16.7 ± 3.2 | 16.6 ± 3.1 | 15.0 ± 2.3 |
| Thromboxam $B_2$ | 3 | 58 ± 11 | 53 ± 15 | 43 ± 17 | 40 ± 11 |
| (mg/ml) | 5 | 49 ± 15 | 51 ± 18 | 35 ± 15 | 37 ± 10 |
| Hypo osmotic pressure | 3 | 61 ± 4 | 72 ± 3 | 65 ± 7 | 67 ± 6 |
| stress recovery test (%) | 5 | 47 ± 5 | 53 ± 4 | 50 ± 5 | 56 ± 7 |
| (Collagen 10 μg/ml + | 3 | 80 ± 7 | 77 ± 4 | 83 ± 5 | 87 ± 5 |
| ADP 10 μg/ml) | 5 | 50 ± 6 | 53 ± 2 | 60 ± 8 | 58 ± 7 |
| Aggregation ability (%) | 3 | 84 ± 7 | 92 ± 2 | 63 ± 10 | 72 ± 9 |
| (Collagen 5 μg/ml) | 5 | 33 ± 3 | 43 ± 7 | 35 ± 7 | 58 ± 15 |
| $CO_2$ partial pressure | 3 | 25 ± 7 | 21 ± 3 | 20 ± 3 | 29 ± 4 |
| (mmHg) | 5 | 12 ± 3 | 13 ± 4 | 13 ± 2 | 22 ± 2 |
| $O_2$ partial pressure | 3 | 71 ± 12 | 66 ± 7 | 87 ± 15 | 88 ± 6 |
| (mmHg) | 5 | 111 ± 13 | 82 ± 9 | 85 ± 11 | 115 ± 18 |
| Bicarbonate | 3 | 4.4 ± 0.3 | 7.2 ± 0.5 | 4.4 ± 0.8 | 12.1 ± 2.3 |
| (mmol/l) | 5 | 2.1 ± 0.8 | 2.9 ± 1.0 | 3.0 ± 0.7 | 8.3 ± 1.6 |
| Platelet morphology | 3 | 25 ± 6 | 33 ± 4 | 27 ± 10 | 25 ± 6 |
| (% of discoidal shape) | 5 | 20 ± 9 | 26 ± 11 | 22 ± 12 | 23 ± 7 |
| Swirling pattern test | 3 | ++ | ++ | ++ | ++ |
| (by the naked eye) | 5 | + | + | + | + | between the two, as is the case in the low osmotic pressure shock recovery test.

From above mentioned test results, either Ex 1 and Ex 2 showed an excellent platelet preservation ability and it was found that the platelet can be preserved in a very close condition as in Comp 2. Especially, Ex 2 showed better results than Comp 2 in a low osmotic pressure shock recovery test (%HSR) and the platelet morphology on day 3 of the preservation and is a very effective platelet preservation solution taking account of the fact that the preservation period is from 3 to 5 days at present.

Example 2

200 ml of the blood was gathered in the blood bag made of polyvinylchloride containing 28 ml of anticoagulant CPD solution and about 20 ml of the platelet preservation solution shown in Table 3 (Ex 3, 4, 5 are the present invention and Comp 3 is the comparative example which is not containing glycerin) was added germ freely to the platelet pellet in the first subsidiary bag, which is prepared by the same method of Example 1. The composition of the CDP solution is the same as Example 1.

TABLE 3-continued

| Composition of artificial platelet solutions (mM) | | | | |
|---|---|---|---|---|
| | Ex 3 | Ex 4 | Ex 5 | Comp 3 |
| $MgCl_2$ | 3 | 3 | 3 | 3 |
| $Na_2HPO_4$ | 33 | 33 | 33 | 33 |
| Na acetate | 25 | 25 | 25 | 25 |
| $Na_3$ citrate | 15 | 15 | 15 | 15 |
| Citric acid | 2 | 2 | 2 | 2 |
| Glucose | — | 25 | 25 | 50 |
| Glycerin | 50 | 25 | 50 | — |
| pH | 7.3 | 7.3 | 7.3 | 7.3 |
| Osmolality(mOsm) | 390 | 390 | 430 | 390 |

After adding each platelet solution to platelet pellet, as same to Example 1, each pellet was placed for 1 hr. at room temperature and then the pellet was floated by shaking (55 strokes/min.) using a horizontal shaking device at 22° C. As the Comparative example (Comp 4), 20 ml of the platelet concentration solution (PC), which was explained in Example 1, was placed in another subsidiary bag. The platelet solutions of Ex 3, 4, 5 and Comp 3 and 4 were preserved for several days. On day 3 and 5, various kinds of tests on the platelet preservation ability were conducted using samples taken from the bag germ freely by connecting operation adapter to the outlet of the bag. The results are shown in Table 4.

TABLE 4

| Platelet function during the preservation | | | | | | |
|---|---|---|---|---|---|---|
| | Days of the preservation | Ex 3 | Ex 4 | Ex 5 | Ex 6 | Comp 3 |
| pH | 3 | 7.05 ± 0.07 | 6.96 ± 0.02 | 6.99 ± 0.03 | 6.98 ± 0.03 | 7.20 ± 0.06 |
| | 5 | 7.24 ± 0.06 | 6.70 ± 0.05 | 6.87 ± 0.04 | 6.83 ± 0.04 | 7.03 ± 0.07 |
| Platelet numbers | 3 | 134 ± 7 | 136 ± 17 | 136 ± 19 | 135 ± 18 | 125 ± 10 |
| ($10^7$/ml) | 5 | 126 ± 6 | 130 ± 17 | 132 ± 20 | 129 ± 14 | 120 ± 10 |
| Mean platelet volume (fl) | 3 | 8.1 ± 0.3 | 8.1 ± 0.4 | 8.1 ± 0.4 | 8.2 ± 0.4 | 8.0 ± 0.3 |
| | 5 | 9.1 ± 0.3 | 8.6 ± 0.4 | 8.6 ± 0.5 | 8.7 ± 0.4 | 8.4 ± 0.3 |
| Glucose | 3 | 771 ± 20 | 9.1 ± 1.7 | 378 ± 18 | 385 ± 21 | 400 ± 20 |
| (mg/dl) | 5 | 725 ± 19 | 6.7 ± 1.1 | 327 ± 17 | 310 ± 25 | 315 ± 27 |
| Lactic acid production | 3 | 4.9 ± 1.3 | 4.4 ± 1.0 | 7.3 ± 1.5 | 6.6 ± 1.0 | 7.6 ± 0.2 |
| amount (mmol/l) | 5 | 9.4 ± 2.3 | 5.1 ± 1.5 | 13.2 ± 2.1 | 11.9 ± 1.9 | 12.3 ± 2.4 |
| β-thromboglobulin | 3 | 9.5 ± 1.7 | 11.5 ± 3.3 | 9.3 ± 2.0 | 8.9 ± 2.3 | 8.5 ± 2.2 |
| (μg/ml) | 5 | 23.2 ± 5.3 | 19.1 ± 4.1 | 16.7 ± 3.2 | 15.5 ± 3.7 | 15.0 ± 2.3 |
| Thromboxam $B_2$ | 3 | 44 ± 12 | 56 ± 10 | 53 ± 15 | 51 ± 16 | 40 ± 11 |
| (mg/ml) | 5 | 47 ± 11 | 49 ± 15 | 51 ± 18 | 48 ± 14 | 37 ± 10 |
| Hypo osmotic pressure | 3 | 61 ± 7 | 61 ± 4 | 72 ± 3 | 69 ± 5 | 67 ± 6 |
| stress recovery test (%) | 5 | 55 ± 4 | 49 ± 7 | 53 ± 4 | 57 ± 6 | 56 ± 7 |
| (Collagen 10 μg/ml + | 3 | 81 ± 5 | 80 ± 7 | 80 ± 6 | 87 ± 6 | 87 ± 5 |
| ADP 10 μg/ml) | 5 | 54 ± 7 | 53 ± 4 | 64 ± 7 | 63 ± 7 | 59 ± 10 |
| Aggregation ability (%) | 3 | 72 ± 6 | 84 ± 7 | 88 ± 8 | 90 ± 5 | 72 ± 9 |
| (Collagen 5 μg/ml) | 5 | 42 ± 4 | 33 ± 3 | 44 ± 10 | 53 ± 6 | 58 ± 15 |
| $CO_2$ partial pressure | 3 | 20 ± 3 | 20 ± 2 | 20 ± 3 | 21 ± 4 | 29 ± 4 |
| (mmHg) | 5 | 11 ± 3 | 12 ± 3 | 13 ± 4 | 15 ± 4 | 22 ± 2 |
| $O_2$ partial pressure | 3 | 98 ± 9 | 104 ± 14 | 92 ± 11 | 100 ± 17 | 93 ± 9 |
| (mmHg) | 5 | 90 ± 11 | 79 ± 11 | 80 ± 7 | 69 ± 14 | 115 ± 18 |
| Bicarbonate | 3 | 6.2 ± 0.9 | 4.4 ± 0.3 | 7.2 ± 0.5 | 5.8 ± 1.1 | 12.1 ± 2.3 |
| (mmol/l) | 5 | 4.4 ± 0.7 | 2.1 ± 0.8 | 2.9 ± 1.0 | 2.6 ± 0.8 | 8.3 ± 1.6 |
| Platelet morphology | 3 | 28 ± 4 | 25 ± 5 | 31 ± 4 | 31 ± 5 | 24 ± 5 |
| (% of discoidal shape) | 5 | 19 ± 4 | 18 ± 7 | 22 ± 7 | 23 ± 5 | 21 ± 3 |
| Swirling pattern test | 3 | ++ | ++ | ++ | ++ | ++ |
| (by the naked eye) | 5 | + | + | + | + | + |

TABLE 3

| Composition of artificial platelet solutions (mM) | | | | |
|---|---|---|---|---|
| | Ex 3 | Ex 4 | Ex 5 | Comp 3 |
| NaCl | 90 | 90 | 90 | 90 |
| KCl | 5 | 5 | 5 | 5 |

The amount of lactic acid production, which can be a measure of anaerobic glucose metabolism of the platelet, as explained in Ex 1, of Ex 4 and 5 is nearly equal to that of Comp 4 and that of Ex 3 was lower than that of Comp 4. Since Ex 3 does not contain glycerin, the MPV (mean averaged platelet volume) became larger than Comp 4 on day 5 of preservation and the swelling of the platelet was observed. As a result of the measurement of β-TG (β-thromboglobulin) and $XB_2$ (thromboxixam $B_2$) as a measure of the activation of the platelet during the preservation, there were no significant differences between Ex 3, 4, 5 and Comp 3 and 4.

On the other hand, Ex 4 and 5 are the platelet preservation solutions which contain both glucose and glycerin and hence it is considered that the platelet was preserved for 5 days in the same level as Comp 4 (commonly used concentrated platelet solution), because of the combined effect of the metabolism of glucose as an energy source and the stabilization of the platelets by glycerin platelet swelling was not observed for Ex 4 and 5 and the flexibility of the platelet membrane at low osmotic pressure (%HSR) was maintained favorably and there were no morphological changes in Ex 4 during 5 days preservation period. Furthermore, as to the pH maintaining effect, both Ex 4 and 5 could maintain pH above 6.8 during 5 days preservation period, and so it is considered that there is no effect of low pH in the platelet function.

From above mentioned examples, in the platelet preservation solution of Ex 3 which does not contain glycerin, the swelling and the decrease in the aggregation of the platelet was observed and morphologically there is a tendency for increase in the activated type after 5 days preservation period. Therefore the preservation ability is not significantly different from that of Comp 4 for 3 days preservation, however it is not adequate for 5 days preservation.

Ex 4 and 5 contain both glycerin and glucose and hence 5 days preservation is possible in the same level as Comp 4.

Example 3

20 ml unit concentrated platelet solution was prepared according to the conventional platelet apheresis method using the blood of a healthy male volunteer and it was divided in two parts (each 10 unit equivalent). One part is used as the plasma preservation solution (PC) (Comp 5 as comparative Example) and the other part was replaced by the platelet preservation solution of Ex 5 shown in the Table 3 and was used as the platelet preservation solution PC (Ex 6 according to the present invention). The platelet preserved for 3 days under the conditions of Ex 6 and Comp 5 was applied a radiation label by $^{51}$Cr and $^{111}$In and the self platelet was transferred for examination. The survival of the platelet after 24 hrs (1 day) and 48 hrs (2 days) were measured. Taking the value at 15 mints after the transfusion as 100%, the survival ratio after 24 hrs and 48 hrs was evaluated by measuring the radioactivity. The results are shown in Table 5.

TABLE 5

| | Survival ratio of the platelet after transfusion | | | |
|---|---|---|---|---|
| | Ex 6 | | Comp 5 | |
| | Day 1 after transfusion | Day 2 after transfusion | Day 1 after transfusion | Day 2 after transfusion |
| Examine 1 | 73.7 | 57 | 70.4 | 55.6 |
| Examine 2 | 80.1 | 71.9 | 68.9 | 56.4 |
| Examine 3 | 64.6 | 44.6 | 74.1 | 52.5 |
| Examine 4 | 88.6 | 65.4 | 86.3 | 63.1 |

TABLE 5-continued

| | Survival ratio of the platelet after transfusion | | | |
|---|---|---|---|---|
| | Ex 6 | | Comp 5 | |
| | Day 1 after transfusion | Day 2 after transfusion | Day 1 after transfusion | Day 2 after transfusion |
| Average: | 76.8 | 59.7 | 74.9 | 56.9 |
| Standard Deviation: | 10.1 | 11.8 | 7.9 | 4.5 |

As shown in Table 5, the survival ratio after the transfusion of the platelet in Ex 6 is 76.8±10.1% after one day and 59.7±11.8% after two days, while that of Comp 5 is 74.9±7.9% after one day and 56.9±4.5% after two days. There are no big differences between Ex 6 and Comp 5 and thus it was confirmed that the platelet can be preserved favorably by the platelet preservation solution of the present invention.

As above explained, the platelet preservation solution of the present invention could maintain the platelet function favorably by stabilization and protection of the platelet membrane by the use of the membrane permeable polyhydric alcohol. The maintenance of the pH was as well favorable and this is a very effective platelet preservation solution taking account of the fact that it showed the preservation ability at the same level as the platelet concentration solution (PC) (Comp 2, 4 and 5). Also by using this platelet preservation solution, it is possible to preserve the platelet without deteriorating the platelet function and to prevent the adverse reactions of the plasma origin. Furthermore, effective utilization and increase in supplying of the plasma as the raw material for the production of plasma fractionated products, such as cryo products, No. VIII factor products and globulin products, becomes possible by the replacement of the major part of the plasma in the platelet concentration solution with the artificial platelet preservation solution of the present invention.

What is claimed is:

1. A platelet preservation solution not containing any plasma proteins and containing 5 to 100 mM of glycerol, from 5 to 15 mM of sodium citrate, from 10 to 30 mM of sodium acetate, from 10 to 50 mM of disodium hydrogen phosphate, up to 10 mM of citric acid, up to 50 mM of glucose and from 50 to 150 mM of electrolyte compounds in addition to said sodium acetate, said disodium hydrogen phosphate and said sodium citrate, wherein said electrolyte compounds include sodium chloride.

2. The platelet preservation solution as defined in claim 1, having a pH of from 6.5 to 8.0.

3. The platelet preservation solution as defined in claim 1, having an osmotic pressure such that a ratio of said osmotic pressure to an osmotic pressure of a normal physiological saline solution comprising NaCl is from 0.5 to 2.0.

4. The platelet preservation solution as defined in claim 1, wherein said electrolyte compounds include at least one ion selected from the group consisting of $Na^+$, $K^+$, $Mg^{2+}$ and $Cl^{31}$.

* * * * *